United States Patent [19]
Polichar et al.

[11] Patent Number: 5,828,726
[45] Date of Patent: *Oct. 27, 1998

[54] PORTABLE, DIGITAL X-RAY APPARATUS FOR PRODUCING, STORING, AND DISPLAYNG ELECTRONIC RADIOSCOPIC IMAGES

[75] Inventors: Raulf M. Polichar; Scott T. Smith, both of San Diego, Calif.

[73] Assignee: Science Applications International Corp., San Diego, Calif.

[*] Notice: The term of this patent shall not extend beyond the expiration date of Pat. No. 5,608,774.

[21] Appl. No.: 773,483

[22] Filed: Dec. 23, 1996

Related U.S. Application Data

[63] Continuation of Ser. No. 494,251, Jun. 23, 1995, Pat. No. 5,608,774.

[51] Int. Cl.$^6$ ...................................................... H05G 1/64
[52] U.S. Cl. .......................................... 378/98.2; 378/98.8
[58] Field of Search .................................. 378/98.2, 98.8, 378/185, 40, 42

[56] References Cited

U.S. PATENT DOCUMENTS

| | | | |
|---|---|---|---|
| 4,383,327 | 5/1983 | Kruger ........................................ | 378/19 |
| 4,593,337 | 6/1986 | Mouyen ................................. | 378/98.8 |
| 4,612,660 | 9/1986 | Huang ...................................... | 378/44 |
| 5,434,418 | 7/1995 | Schick ..................................... | 378/98.8 |
| 5,452,337 | 9/1995 | Endo et al. ................................. | 378/4 |
| 5,454,022 | 9/1995 | Lee et al. ............................... | 378/98.8 |
| 5,608,774 | 3/1997 | Polichar et al. ........................ | 378/98.8 |

FOREIGN PATENT DOCUMENTS 0429977  11/1990  European Pat. Off. .

OTHER PUBLICATIONS

Street, et al., "Charge–Coupled Devices and Solid State Optical Sensors IV", *SPIE*, 2172:144–154 (Feb. 7–8, 1994).
Street, et al., "Amorphous Silicon Arrays Develop a Medical Image", *IEEE*, pp:38–42 (Jul. 1993).
Tannas, "Evolution of Flat–Panel Displays", *Proceedings of the IEEE*, 82:4, pp. 499–509 (Apr. 1994).
Antonuk, et al., "Considerations for High Frame Rate Operation of Two–Dimensional a–Si:H Imaging Arrays", *Materials Research Society Symposium Proceedings*, 297:945–950 (1993).
VIDISCO, Ltd., Sales Brochure for "A–500E Portable Video Based X–Ray Inspection System" (1994).

*Primary Examiner*—Don Wong
*Attorney, Agent, or Firm*—Fitch, Even, Tabin & Flannery

[57] ABSTRACT

A portable, self-contained, electronic radioscopic imaging system uses a pulsed X-ray source, a remote X-ray sensor, and a self-contained, display and controller unit to produce, store, and/or display digital radioscopic images of an object under investigation. The pulsed X-ray source transmits a burst of narrow pulses of X-rays at the object being investigated at a low repetition rate. The X-ray sensor utilizes an X-ray scintillating screen in combination with either an integrating CCD camera, or an active matrix of thin film transistors and sample-and-hold photodiodes, to produce an integrated signal representative of the accumulated number of flashes of radiation (X-ray pulses that pass through the object) that are sensed in a given pixel area of the scintillating screen. The self-contained display and controller unit utilizes digital signal processing within an enhanced portable computer, including a flat solid state display panel and associated drive circuitry, in order to display the full dynamic range and resolution of the sensor. A modem allows the digitized image to be sent to a remote location where the exact same image can be recreated for analysis by off-site experts.

7 Claims, 8 Drawing Sheets

PORTABLE, DIGITAL X-RAY APPARATUS FOR PRODUCING, STORING, AND DISPLAYNG ELECTRONIC RADIOSCOPIC IMAGES

This application is a continuation of application Ser. No. 08/494,251, filed Jun. 23, 1995, now U.S. Pat. No. 5,608,774.

BACKGROUND OF THE INVENTION

The present invention relates to a portable, self-contained, X-ray apparatus that digitally processes, displays, stores, and/or transmits electronic radioscopic images of sealed packages, containers and other objects on location for security, customs, and other non-destructive purposes. For example, one application for the present invention is to determine if a closed suitcase or sealed package contains a bomb or contraband.

There are many instances in the security or customs field when it is necessary to examine or inspect, in a non-destructive way, the contents of a closed package, box, suitcase, or other container. For example, customs departments are routinely charged with the responsibility of inspecting the contents of incoming packages to make sure such packages do not contain explosives, drugs or other contraband. Similarly, terrorists, criminals, or other enemies frequently carry out their criminal acts of terrorism or war by planting bombs in sealed containers or packages, and then sending the sealed containers/packages to the intended victims, e.g., through the mail, or planting the sealed container/packages at the desired target, e.g., by leaving a locked suitcase or a sealed box containing a bomb in a busy public transportation terminal. When security personnel encounter suspicious packages or other containers being sent through the mail, or left at public transportation terminals, or other locations, they must perform a careful inspection of such containers to ascertain their contents.

When suspicious containers, such as suitcases, sealed boxes/packages are discovered, they generally must be examined or inspected on location in a non-destructive manner. If the non-destructive examination reveals the presence of explosives (e.g., a bomb) or contraband (e.g., drugs), then the container and its contents must be safely disposed of. If, on the other hand, the examination reveals the absence of explosives or contraband, then the container may be handled in a normal manner, i.e., forwarded on to its owner or addressee.

Unfortunately, the process used to examine or inspect a suspicious sealed box, package, suitcase or other container must not trigger any bomb that may be concealed inside. Thus, for example, as a safety precaution, the suspicious container may not be opened because such opening may trigger any bomb contained therein. Similarly, the suspicious container may not be moved because such movement could likewise trigger a hidden bomb. Further, the suspicious container may not be examined with high doses of radiation because such radiation, if significantly greater than normal background radiation, could also trigger a hidden bomb. What is needed, therefore, is a non-invasive technique for inspecting the contents of a suspicious container without requiring that the container be opened, moved, or subjected to high levels of radiation.

Heretofore, suspicious containers of the type referenced above have been examined using portable, generally low power, X-ray generators and highly sensitive X-ray film as a detector, with many attendant problems. For example, the film used with such conventional film-based radiography systems has a poor shelf life in the environment typical to field inspections, which means that its sensitivity may vary considerably. The operator must then go back to the object under test for each image taken until the correct exposure and orientation is obtained. Once such image is taken, it must then be processed with a portable chemical laboratory with the attendant delays of such efforts.

It is also known in the art to improve the conventional film-based radiography systems by adapting certain types of industrial imaging systems as an image detection system to overcome some of the field problems. Such systems typically use intensified, low-light level cameras to record the image, and then conventional cathode ray tube (CRT) monitors to display the resulting X-ray images. Unfortunately, such systems are bulky and poorly suited for portable applications. Further, the CRT displays do not always provide the contrast needed to readily see the X-ray image in bright ambient light conditions. Further, while some limited image enhancement techniques have been applied to such existing systems, the output image is still simply a real-time analog CRT image.

SUMMARY OF THE INVENTION

Broadly, and in general terms, a goal of the present invention is to provide a completely digital system capable of recording and digitizing the individual X-ray image data, including the ability to store and retrieve that data onto a suitable storage medium, such as a hard disk of a portable computer, and using such portable computer as a controller for selectively displaying the image in a way that reveals the full dynamic range and resolution of the sensor, and/or transmitting the image to remote locations (when necessary) via a modem for evaluation by experts who are not on site.

The present invention addresses the above and other goals by providing a portable, self-contained, electronic radioscopic imaging system. The system is made up of three main subsystems: (1) a pulsed X-ray source, (2) a remote X-ray sensor, or "imager", and (3) a self-contained, display and controller unit, or "display/control unit." The pulsed X-ray source transmits narrow pulses of X-rays at the object being investigated at a low repetition rate. The X-ray sensor or imager utilizes a scintillating screen that produces flashes of light when impinged by an X-ray in combination with either an integrating CCD camera, or an active matrix of thin film transistors and thin film sample-and-hold photodiodes, to produce an integrated signal that represents the sum of a prescribed number of flashes of radiation that pass through the object in a given pixel area. The self-contained display and control unit utilizes digital signal processing within an enhanced portable computer, including a solid-state flat panel display and associated drive circuitry, in order to display to an operator the full dynamic range and resolution of an image-capturing novel sensor utilized within the imager. A modem further permits the digitized image to be sent to a remote location where the exact same image can be recreated for analysis by off-site experts.

In a preferred embodiment, the X-ray source may be a commercially available, portable, pulsed X-ray source that, on direct command from the controller, puts out a sequence of short pulses of radiation, at rates of, e.g., about 6 to 25 per second, with duration times of approximately 50 nsec/pulse. Such pulses are directed at the object under investigation and are recorded, at the opposite side of the object, by the imager, or solid-state imaging system. The intensity of the individual pulses is preferably of such low power as to be insufficient to fully excite the solid-state sensor(s) that forms the heart of the imager. In order to still detect and create an image with such low power X-rays, the present invention includes the ability to sum (or integrate) the effects of the series of pulses directly on the individual pixel photosites of the recording device itself. That is, the imager sensor is capable of integrating the X-ray flux and maintaining the resulting charge distribution for several seconds until the accumulated X-ray flux is sufficient to provide a signal producing a full-scale image. After the X-ray pulses have ceased, a time integrated signal is thus available to be read out of the imager and provided to the display/control unit for further processing. Advantageously, by using pulses and integrating such pulses for a prescribed time period in this fashion, the need for complex and power-consuming off-chip integration circuitry in the display/controller unit is avoided. Further, the possibility of induced electrical noise from the X-ray source itself is minimized.

In accordance with one aspect of the invention, two versions of the "imager" may be included as part of the imaging system. A first version utilizes a conventional CCD (charge coupled device) camera, whose normal charge readout is inhibited during the integration period, and which views an X-ray conversion screen (e.g., an X-ray scintillation screen) through an efficient optical lens/mirror system. The second version uses a flat panel, amorphous silicon, photo-sensor, in direct contact with an X-ray scintillation screen. In both versions, the image signal from the X-rays is built up in the sensor photosites until the exposure is completed. Data from the X-ray sensor, referred to herein as the "integrated signal," is then read out on command to the display/control unit. Advantageously, during such readout, the display/control unit need not be positioned next to the object being examined, but may be positioned some distance therefrom, e.g., behind a safety shield or wall. As a further advantage, the integrated signal may be read out in a format that is compatible with the processing and enhancement of digital images, i.e., in a format that can be used directly by the display/control nit, such as in the RS-170 video standard.

The first version of the solid-state sensor is the simpler and less costly approach, but requires a larger volume than does the second version in order to house the optical path and CCD camera and related circuitry. The second version (flat panel) advantageously provides an X-ray sensor that is almost as thin as a normal film cassette, and can thus be inserted into narrow places where the lens/mirror/CCD sensor would not fit without moving the object being examined. Because the inspection of unknown packages is often best and safest done without disturbing the package, the second version, although more costly, is generally the preferred version.

In operation, the display/control unit generates appropriate control and trigger signals that synchronize the operation of the X-ray source, the integration of the image onto the X-ray sensor, and the downloading of the integrated signal to the display/control unit. At the display/control unit, the image information contained within the integrated signal is processed, as required, and is displayed on a solid-state flat panel display in high-resolution computer graphics format. One feature of the invention allows the displayed image to be overlaid with additional information stored in the computer using a chroma key encoder that permits image data to be replaced with character overlays in specific areas of the image.

The display/control unit is a self-contained package, typically housed to look like a suitcase, that holds a small, single board computer operating in a Windows environment. The unit includes a built-in, monochrome, active matrix, solid-state, flat-panel display. The active matrix flat panel display (FPD) is used not only to view the image of the object under investigation, but also serves as a computer display, or computer "screen," to convey certain annotations and messages directly from the computer. An auxilliary image processor included within display/control unit allows two independent video streams—one comprising the sensed image obtained from the processed integrated signal, and the other comprising graphic information generated by the computer—to be combined for display on the FPD. Such image processor includes an image memory wherein the sensed image signal may be stored. The normal Video Graphics Adapter (VGA) of the computer is passed through the image processor where the two independent video streams are combined using the chroma key technique referenced above. A specific color code is defined which causes the contents of the image procesor memory to be displayed rather than the computer generated graphics. Computer generated graphics employing colors other than the chroma-dey color are passed to the FPD directly.

The personal computer is further equipped with a hard disk drive to store programs and demonstration images. The computer also has a built-in modem capable of transmitting the digital images over a phone line, or equivalent telecommunications link, e.g., an RF digital link, for remote inspection of the image.

The auxiliary image processor (included in the same suitcase-type housing in which the single board computer is housed) receives the integrated signal generated by the X-ray sensor and processes it to produce video RGB (red-green-blue) output signals. Such RGB signals are then converted by a special driver circuit to the appropriate codes used by the monochrome active matrix display panel to allow the information contained in such signals to be displayed on the FPD. Advantageously, this approach allows up to 256 independent gray levels of contrast (i.e.,8 data bits) to be displayed on the included monochrome FPD. Look-up tables permit a user to work with larger data sets and then to use the most significant bits for the displayed image. Typically, the display will be in the same format as the VGA resolution, which means it is usually non-interlaced and of higher resolution than a conventional video signal.

In accordance with another feature of the invention, the display/control unit is further equipped with a conventional floppy disk drive as well as a PCMCIA interface. Normal image storage may be made on conventional floppy disks using the floppy disk drive. The PCMCIA interface permits the attachment of removable mass storage (e.g., a removable hard disk) and other peripherals. The feature of removable media allows a user to collect many images, and then take them to a remote location where they can be played back on a remotely located computer, or simply filed for archival purposes. Advantageously, the display/control unit (which also powers the imager) may be powered from either enclosed rechargeable batteries, or via the standard ac power lines (50/60 Hz; 110 or 220 VAC).

Exposure control and manipulation of the images obtained using the system of the present invention is controlled by a software program designed, in the preferred embodiment, to operate in the MicroSoft Windows environment. All functions of the system are thus available as either icon buttons or through pull-down menus. The image that is obtained of the object under investigation is in the form of a "client" window within a "parent frame" which houses menu, icon, and status bars bordering the display. All functions are set using a built-in pointing device or an alphanumeric keyboard. Functions include the firing of the X-ray source (with safety delay, if desired), the selection of the integration interval, modification of the displayed contrast, magnification of the displayed image (complete with panning and scrolling within the zoomed or magnified area), digital sharpening of the image, point-to-point measurements, annotation of the image, storage and retrieval of stored images, and correction of the orientation of the image to correct for differing operating positions of the X-ray sensor. Images may be stored and retrieved from the internal hard disk, the built-in floppy drive, or from a removable hard drive plugged into the PCMCIA interface. Operator safety is provided with a removable safety key that inhibits the fire and integrate signals from the computer within the display/control unit when a key switch is turned off and removed. An additional safety key is provided as part of the X-ray source. Further, a displayed warning comes up each time a new image is taken alerting the operator that the X-ray source is about to be activated, and requires a second keystroke to acknowledge such warning before the X-ray source can be triggered to fire.

It is a feature of the present invention to provide a high-resolution, solid-state imaging system that utilizes on-chip light integration in order to eliminate the need for intensifying electro-optic components, and that prevents noise from the X-ray source from being mixed with the image signal when it is digitized.

It is a further feature of the invention to provide such an imaging system that is based on a personal-computer controller for acquiring, displaying, storing and/or transmitting the digital image obtained using a pulsed X-ray source and integrating X-ray sensor.

It is another feature of the invention to provide such an imaging system that utilizes digital processing to enhance contrast, improve sharpness, and correct for system and/or source geometry artifacts.

It is yet an additional feature of the invention to provide a personal-computer controlled imaging system that utilizes a separate image processor/digitizer for faster processing of the image data and to provide freedom from the limitations of the computer display data formats.

It is a still another feature of the invention to provide an imaging system that allows image data to be stored on removable digital storage media.

It is another feature of the invention to provide a digital imaging system that utilizes chroma-key overlays that permit computer data to be overlaid directly on the displayed image.

It is a further feature of the invention to provide a portable digital imaging system that uses a flat panel display that provides a full contrast range and sensitivity over a wide range of ambient light conditions, from dim room light to bright sun-light.

It is a further additional feature of the invention to provide a personal-computer based imaging system that uses Windows-based PC software with icon-based functions accessible by built-in pointing devices.

It is also a feature of the invention to provide a self-contained digital-based imaging system that includes a built-in modem or equivalent digital communication device to permit transmission of image data to a remote site over phone lines, RF links, or other telecommunication channels, for interpretation at the remote site.

It is another feature of the invention to provide an X-ray imaging system for investigating suspicious packages, or other objects, wherein the control of the X-ray source and the camera integration is interlocked under system software and/or mechanical key switches.

It is still a further feature of the invention to provide an X-ray imaging system that is portable and self-contained, including batteries, so that it can be easily carried on-site and set up at the location of the object to be investigated without having to move the object to be investigated.

BRIEF DESCRIPTION OF THE DRAWINGS

The above and other aspects, features and advantages of the present invention will be more apparent from the following more particular description thereof, presented in conjunction with the following drawings and appendix wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 5:
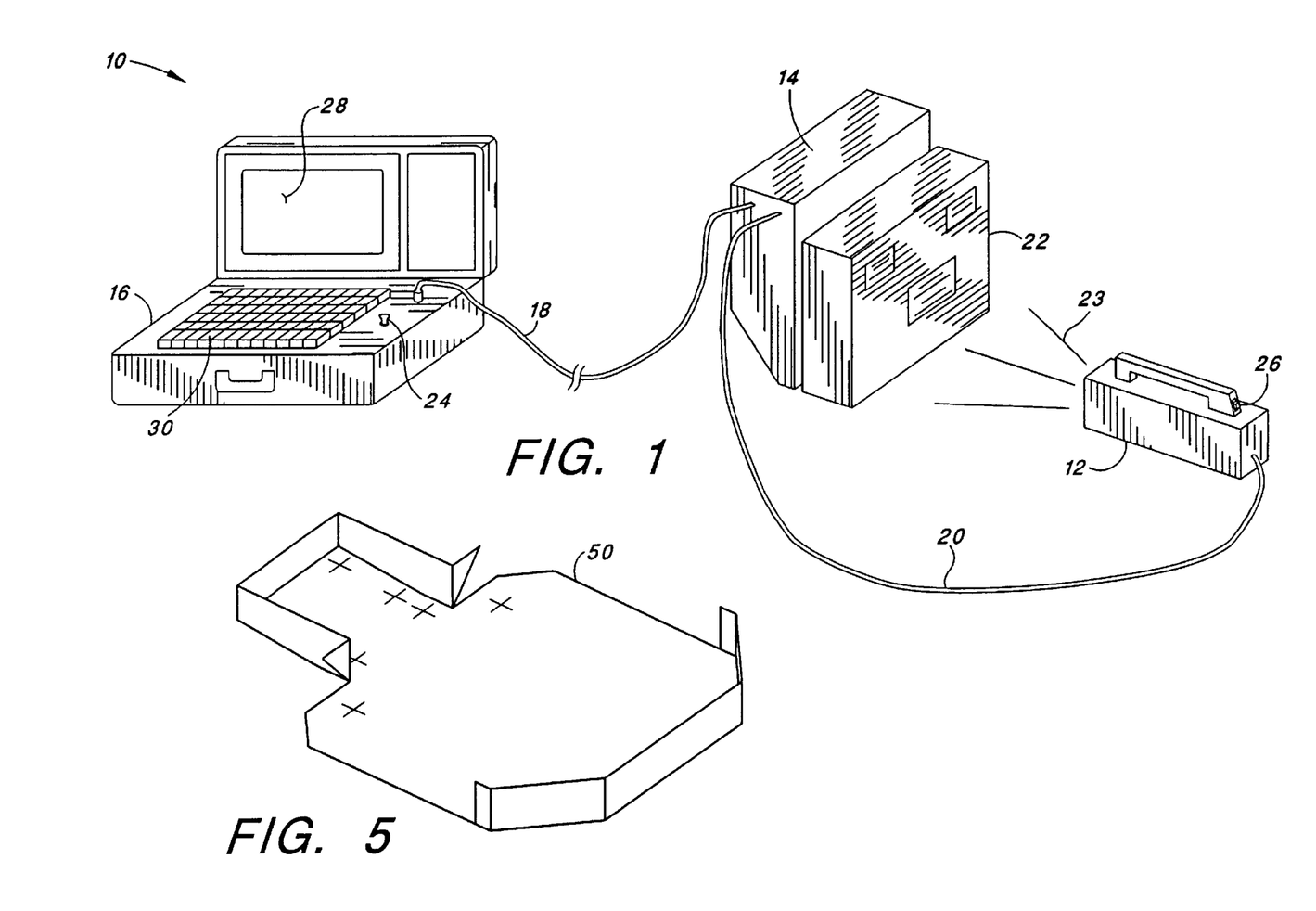
FIG. 1 depicts the three main subsystems of the imaging system of the present invention as it is used to form a radiograpahic image of a package under investigation.
FIG. 5 is a perspective view of a special shield that is used to shield the CCD camera included in FIG. 3A.

Turning first to FIG. 1, there is shown an imaging system 10 made in accordance with the present invention. The system 10 includes three main subsystems: (1) a portable X-ray source 12, (2) an imager 14, and (3) a Display/Control Unit 16. The three subsystems are interconnected with two cables. A first cable 18 is a "long" cable and is connected between the Display/Control unit 16 and the imager 14. The long cable may be as long as 180 feet. A second cable 20 is a "short" cable that is connected between the imager 14 and the X-ray source 12. The short cable is typically less than 10 feet in length.

Advantageously, the system 10 is portable, which means it is sufficiently lightweight and non-bulky to enable a single person to hand-carry its three constituent subsystems and associated cables to a field location where an object 22 to be investigated is located. Once on site, the system 10 is designed to: (1) facilitate quick and easy setup around the object 22 to be investigated, (2) provide rapid image acquisition at the field location, and (3) provide image enhancement tools that aid in the evaluation of the acquired image.

In operation, the system 10 is setup by placing imager 14 next to the object 22 to be investigated, e.g., as close as possible to the object. The X-ray source 12 is then placed, e.g., two to three feet from the imager 14, on the opposite side of the object 22. The display/control unit 16 is then connected to the imager by way of the long cable 18 and is placed a safe distance from the object 22. The X-ray source is also connected to the imager 14 by way of the short cable 20. When everything is properly connected, all three subsystems are turned on, and under control of the display/control unit 16, the X-ray source 12 generates a pulsed X-ray beam (represented by the lines 23) that is allowed to pass through the object 22. The pulsed X-rays pass through respective segments of the object 22 with varying degrees of intensity, or energy, as a function of the contents of the object 22, and are captured or sensed at corresponding pixel areas of the imager 14. The intensity or energy of these pulses that pass through the object 22 are accumulated or summed (integrated) over the duration of the pulsed beam (exposure time), which exposure time may include, e.g., a burst of 15–99 pulses.

At the conclusion or termination of the pulsed beam, the imager 14 has acquired an integrated or summed energy for each pixel of the display area, with the combined collection of all such energies for all the pixels comprising an integrated image signal. The integrated image signal is then transferred to the display/control unit where it is appropriately processed and displayed. Such processing includes digitizing the signal to facilitate its subsequent storage, retrieval, enhancement, display and/or transmission.

Advantageously, the system 10 is designed for safety and ease of operation. X-ray safety is assured, e.g., through the use of the pulsed X-ray source 12. Such pulsed source produces extremely short bursts of X-rays capable of penetrating several inches of most materials, yet generates extremely low radiation dose (integrated exposure) levels outside the direct source beam. Safety is further enhanced by two interlock keys, both of which must be in place and in the "ON" position in order for the X-ray source 12 to be activated. A first interlock key 24 is at the display/control unit 16. A second interlock key 26 is at the X-ray source 12. Moreover, a software interlock is provided as part of the operation of the display/control unit 16. Such software interlock generates and displays a warning message on a screen 28 on the display/control unit 16 and then requires the operator to acknowledge such warning message by pressing a key on a keyboard 30 of the display/control unit 16 before the X-ray source can be triggered.

An additional safety feature is provided through the use of the long cable 18 which permits the display/control unit 16 (and hence the operator) to be located a safe distance (the length of the cable 18) from the object 22 being investigated. The cable 18, for example, may be as long as 180 feet, although in the preferred embodiment it is only about 60 feet (typically provided through two 30-foot sections). The cable 18 could be made even longer, if desired, if appropriate line drivers are inserted into the line at regular intervals, and/or if a different transmission medium is used (e.g., fiber optic cable, and or RF wireless transmission).

Figure 2:
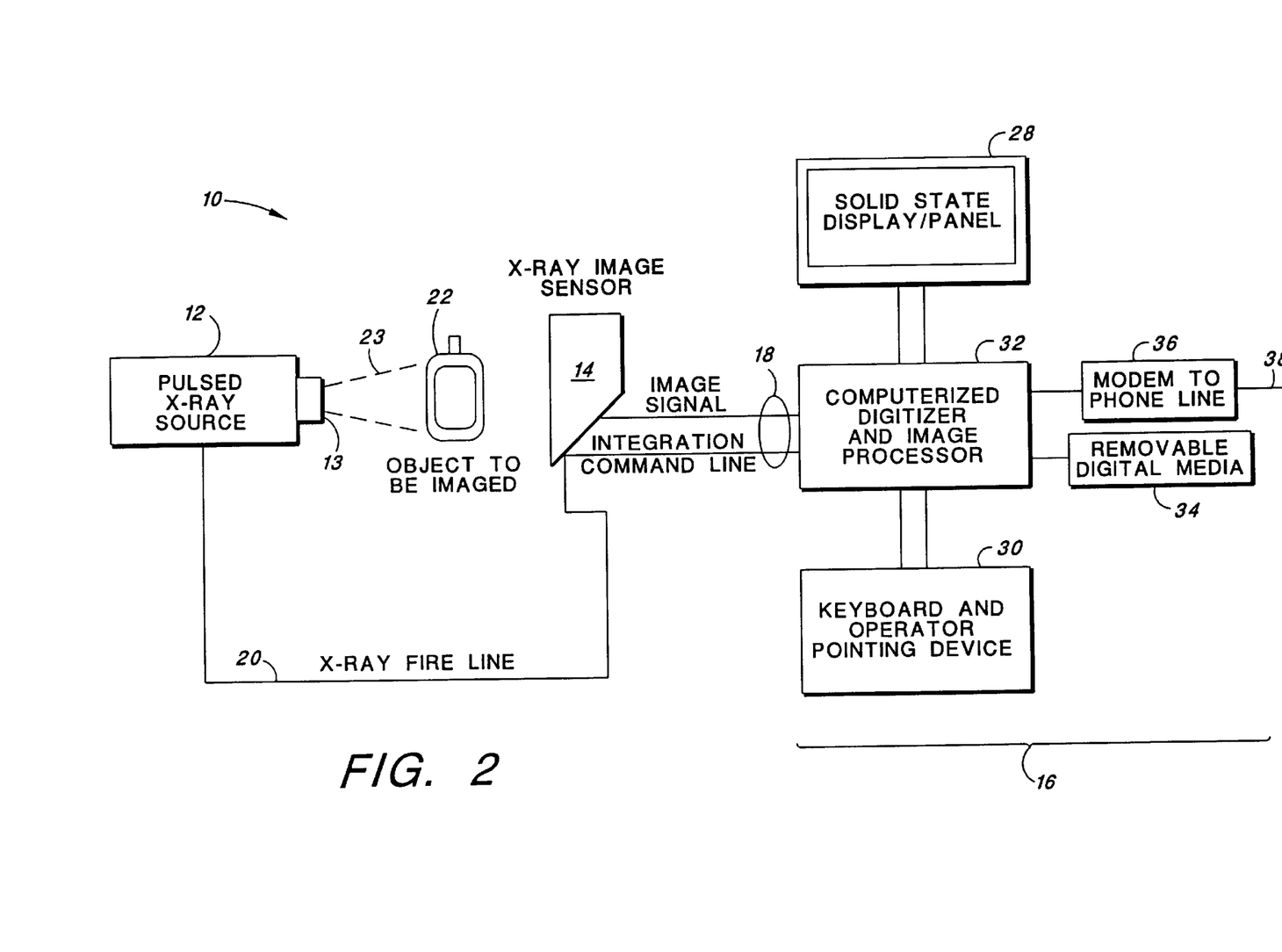
FIG. 2 is a block diagram of the imaging system.

Turning next to FIG. 2, there is shown another diagram of the imaging system 10 which illustrates, in block diagram form, essentially the same elements as are depicted in FIG. 1. However, FIG. 2 shows further detail of the display/control unit 16 (which hereafter may be referred to as simply the "control unit 16"), and in particular shows that the control unit 16 includes a computerized digitizer and image processor 32, a solid state display panel 28, a keyboard and operator pointing device 30, removable digital media 34, and a modem 36 to allow connection to a phone line 38. The long cable 18 connects between the computerized digitizer and image processor 32 and the imager 14 (sometimes referred to herein as an "X-ray sensor"). The signals sent and received over the long cable 18 include the integrated image signal and a trigger signal, as well as an operating voltage (power) for the imager 14. The trigger signal triggers both the integration circuitry within the imager 14 as well as the X-ray fire line going to the pulsed X-ray source via the short cable 20.

Advantageously, the pulsed X-ray source 12 may be realized using any suitable commercially available X-ray source. One commercially available X-ray source that may be used within the system 10, for example, is the Golden Inspector® Model 200 X-ray source manufactured by Golden Engineering Inc., P.O. Box 175, Centerville, Ind., 47330, the operator's manual for which is incorporated herein by reference. The Inspector Model 200 X-ray source has a maximum output energy of 150 kV, and produces about 3.0 mRem output dose per pulse at one foot (on the beam centerline, with 2.5 mm aluminum filter). It includes a built-in electronic counter to provide from 0–99 pulses. The X-ray pulses that are generated have a nominal pulse width of 50 nanoseconds. The nominal pulse rate is 20–25 pulses per second (pps). It is a modular design having approximate dimensions of 4.2 inches wide by 4.2 inches deep by 15 inches long. It weighs only 20.5 pounds with a battery. It also includes a standard camera tripod mounting plate (¼-20 thread). Besides a battery, it includes a power cord and self-contained 29 volt rechargeable battery pack. The source 12 may be battery operated or it may be plugged into a 110/220 VAC, 50/60 Hz power outlet using conventional power cords. Switching between battery and line power is automatic. Other equivalent portable X-ray sources could, of course, be used in lieu of the Golden Inspector Model 200 X-ray source.

The X-ray source 12 should be positioned so that the beam centerline intercepts the "imager screen" near its center. The imager screen is that portion of the imager 14 designed to be impinged by the pulsed X-rays that pass through the object 22, and hence that portion of the imager which captures the X-ray image. One of the advantages of using the modular X-ray source 12 is that it can be readily adjusted in height and orientation by positioning it on the floor, on risers, or on an adjustable platform, as required. The imager 14 may also be adjusted, as required, so that the region of interest of the object 22 is as close as possible to the imager screen. The location of the imager screen on the imager 14 may be denoted by a rectangular indentation on the face of the imager 14, or by other suitable markings (e.g., painted lines). The X-ray source is preferably positioned approximately two to three feet from the imager screen for best image results.

It is also preferred that a suitable X-ray source beam filter 13 (FIG. 2) be used with the X-ray source 12 in order to enhance the quality (resolution and contrast) of the resulting image. An X-ray filter typically comprises a thin metal sheet that is placed over the exit aperture of the X-ray source to remove by absorption and scatter a fraction of the low energy X-rays. It has been found that, depending on the thickness and material composition of the object imaged, very low energy X-rays in the source beam may not be contributing to the formation of the X-ray image formed (which X-ray image is, in essence, an X-ray "shadow" of the object(s) placed in the path of the X-ray beam) by transmission through the object. These low energy X-rays, however, are believed, in some instances, to decrease the quality of the image by contributing to statistical noise, thereby resulting in a decrease in image resolution and contrast through scattering. Hence, the filter 13 is used to remove such low energy X-rays. The type and thickness of the filter 13 to be used typically depends on the thickness and composition of the object.

When imaging a thin, or lightweight target, the filter 13 should be of minimal thickness, such as 0.005 to 0.010 inch thick copper or 0.020 to 0.030 inch thick aluminum. If the target 22 contains dense materials, a more substantial filter 13 may give better results. A copper filter of 0.020 inch thickness may help image effectively steel objects. Alternatively, use of a 0.050 inch thick aluminum filter is also believed to produce satisfactory results.

The problem of imager saturation, sometimes referred to as "blooming", can be corrected by decreasing the exposure time. It has also been learned that imager saturation can be lessened using a suitable beam filter 13. When trying to image objects which have adjacent areas of high and low density materials, saturation of the less dense regions can hide detail in the dense areas. By employing the different thicknesses of filtering materials, it has been found possible to reduce or even eliminate this "blooming" problem, reduce noise due to scattering, and produce a more detailed radioscopic image.

Figure 3A:
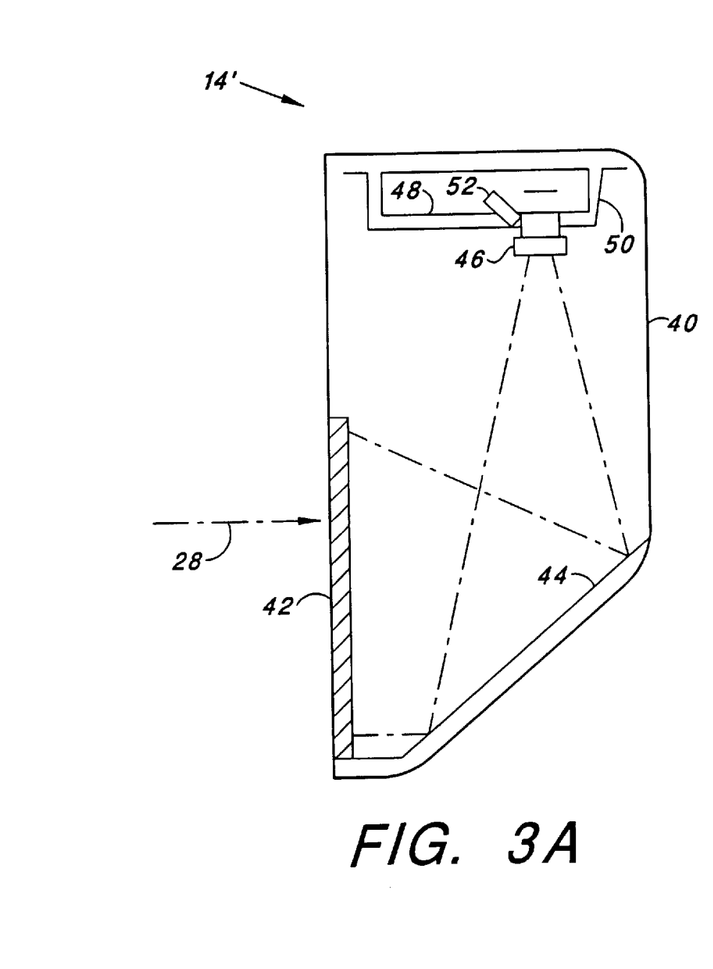
FIG. 3A illustrates a CCD camera version of the X-ray sensor that may be used with some embodiments of the system of FIGS. 1 and 2.

The imager 14 is realized by application of a suitable X-ray sensor. One type of X-ray sensor that may be used for the imager 14, for example, is an integrating CCD camera subsystem 14' modified in accordance with the present invention, as shown in FIG. 3A. As seen in FIG. 3A, the CCD subsystem 14' includes a lightweight metal housing 40, e.g., made from 0.06 inch thick aluminum, that holds an X-ray light converter screen 42, which screen 42 functions as the "imager screen" referred to above. Typically, the screen 42 is eight by ten inches in size, and is realized using a suitable scintillating screen, e.g., a phosphorus scintillating screen. As the X-rays strike a particular pixel area of the scintillating screen 42, flashes of phosphorescence occur having an intensity or energy proportional to the energy of the X-ray beam. Such flashes are then optically guided through a suitable optical path, which includes a front surface mirror 44, through a fast lens 46, to a solid-state, compact, integrating charge-coupled device (CCD) camera 48.

The image is recorded within the CCD camera 48, and is converted to a standard video signal that is sent to the control unit 16 via the long cable 18 (FIGS. 1 & 2). The housing 40, in the preferred embodiment of the imager 14', includes a built-in handle to help transport it. Such handle may also be positioned to help hold or support the housing so that the screen may be maintained in a generally vertical position when the imager 14' is oriented as shown in FIG. 3A.

A preferred imager 14' has approximate dimensions of 10.3 inches wide by 12 inches high and 7 inches deep. The weight of the imager 14' is under 10 pounds. Operating power for the imager 14' is obtained through the cable 18 from the control unit 16, and is typically provided by way of a power supply voltage of 12 volts. Hence, like the other components of the overall system 10, the imager 14' is readily portable and easy to use at an on-site field location.

As indicated previously, the CCD camera 48 integrates the image over a prescribed number of X-ray pulses (exposure time). Advantageously, the integration of the light image (resulting from the flashes of phosphorescence that occur as the X-ray pulses impinge the scintillating screen) occurs on the CCD chip, as opposed to being carried out using off-chip electronic circuitry. The normal charge readout is inhibited during the integration period, thereby making such charge readout available at the completion of the integration period for use as the standard video signal, or integrated signal, previously referenced. Further, integration only occurs in synchrony with the generation of the burst of X-ray pulses, thereby effectively blocking out "noise" that is present at times other than when the X-ray burst is present.

In the preferred embodiment of the imager 14', the CCD camera 48 is realized using an 1100 Series Board Level Monochrome CCD Camera obtained from Cohu, Inc. 5755 Kearny Villa Rd., San Diego, Calif., 92123. The 1100 Series CCD cameras feature a ½ inch-format on-chip microlens sensor, mounted to an electronic board whereon supporting electronic circuitry is placed, such as driver circuits, video generation circuits, power supplies, and the like. Advantageously, the 1100 Series cameras may readily be configured for custom purposes. In this instance, the only significant modification that needs to be made to the 1100 Series CCD Camera obtained from Cohu is to change the integration time of the camera from being controlled by a start/stop pulse, to being controlled by an exposure time (number of pulses) so that integration occurs only during the pulsed X-ray burst, and not at other times. Even this modiciation would not be required is one chose to generate a separate start/stop pulse coincident with the beginning and ending of the exposure time. However, by making the modification indicated above, the need for such a separate start/stop pulse is eliminated, thereby reducing the number of signals that need to be communicated through the long cable 18.

With a Series 1100 CCD camera (or equivalent camera where a microlens sensor is mounted on an electronic board), it has been found that the CCD camera 48 needs to be protected from exposure to ionizing radiation damage. Two types of problems may arise. First, X-rays which penetrate the imager 14' without interacting with the scintillating screen 42 may strike the CCD chip of the camera 48. If this happens, visible specks of white light appear on the image, thus reducing the image quality. Second, prolonged exposure to such radiation can prove to be harmful to the integrated circuit components, e.g., the CCD chip or other integrated circuits used to generate the video signal, possibly resulting in failure of such circuits.

In order to reduce the number of X-rays that strike the camera 48, the camera 48 is encased in a 0.125 inch thick lead housing or shield 50. The preferred shield 50, for use with the particular CCD camera 48 specified above, is shown in its folded state in FIG. 5, before placing it around the CCD camera 48. In addition, a 0.25 inch thick lead plate 52 may be placed between the CCD-chip and incident X-ray radiation in order to further shield the CCD chip from stray X-rays.

A further aspect of the invention concerns the use of the first surface of the mirror 44 (FIG. 3A) to direct the image of the scintillating screen 42 to the CCD camera 48. Employing the mirror 44 as shown, i.e., in line with the X-rays that strike the scintillating screen, permits placement of the CCD camera 48 at a location outside of the main X-ray path, thereby significantly reducing the number of X-rays that might otherwise directly strike the CCD camera or its associated electronic components. (Note, any X-rays that pass through the scintillating screen 42 would also pass through the mirror 44.)

As indicated, the preferred CCD camera 48 is an 1100 Series CCD camera made by Cohu of San Diego, Calif. Representative specifications of the Cohu's 1100 Series camera are as follows:

| Pick Up Device: | ½" Interline transfer, microlens sensor |
| --- | --- |
| Active Picture Elements: | RS-170: 768 (H) × 494 (V)<br>CCIR: 752 (H) × 582 (V) |
| Pixel Cell Size: | 8.4 μm (H) × 9.8 μm (V) |
| Total Pixel Elements: | 811 (H) × 508 (V) |
| Resolution: | RS-170: 580 horzizontal TVL, ≧350 vertical TVL |
| Synchronization | Horizontal and Vertical Crystal (RS-170) Asynchronous reset |
| Shutter | 1/60 to 1/10000 |
| Power | 12 VDC, 3.6 W max |
| Size | 1.75 × 3.88 × 1.00 inches |

Figure 3B:
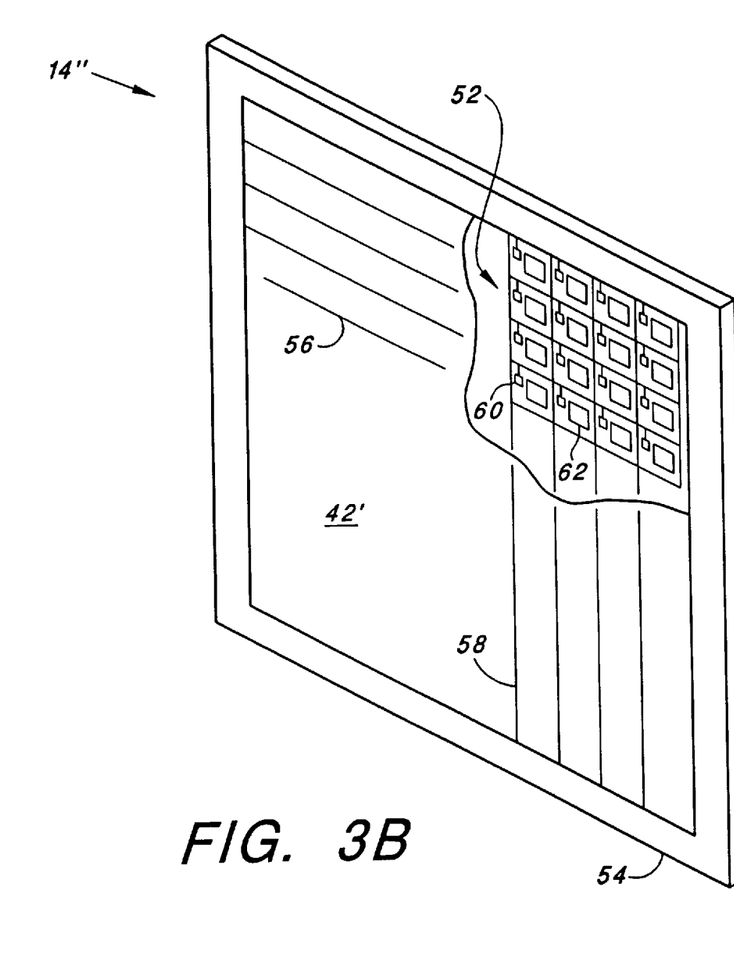
FIG. 3B depicts a TFT flat panel amorphous silicon X-ray sensor that may be used with other embodiments of the system of FIGS. 1 and 2.

Another type of X-ray sensor that may be used as the imager 14 is a flat panel sensor 14", as shown in FIG. 3B. Such sensor 14" offers the advantage of being flat and relatively thin so that it can be positioned into tight spots, and further eliminates the need for a mirror(s) and/or lenses to define an optical path. The sensor 14" includes a conventional X-ray scintillation screen 42' that is in direct contact with a flat panel, amorphous silicon, TFT (thin film transistor) photo sensor 52. The TFT photo sensor 52 is made on a glass or ceramic substrate 54, and includes a matrix of thin film transistors 60. Each TFT further has its own thin film sample and hold (S&H) photodiode 62 associated therewith. The matrix of TFT's and S&H diodes is sufficiently dense so that each TFT 60 and associated S&H photodiode 62 corresponds to a different pixel of the sensor 14". The S&H photodiode 62 senses abd accumulates all of the light flashes produced at the corresponding pixel of the scintillation screen 42' during the integration time. At the end of the integration time, the accumulated signal at each pixel site that is held by the corresponding S&H photodiode 62 is read through its corresponding TFT transistor 60 through appropriate row drive electronics 56 and column drive electronics 58, in conventional manner. Such accumulated signals, for all of the pixels of the sensor 14", thus comprise the integrated image signal for a given exposure time.

Further details of the manner of making and using a flat panel sensor of the type illustrated in FIG. 3B as the sensor 14" are described, e.g., in Street, et al., "Amorphous Silicon Arrays Develop a Medical Image," *IEEE Circuits and Devices*, pp. 38–42 (July 1993); and Wu et al., "Imaging With Page-Sized A-Si:H 2-Dimensional Sensor Arrays," *SPIE Proceedings*, Vol 2172 pp. 144–154. Both of these references are incorporated herein by reference.

Figure 4:
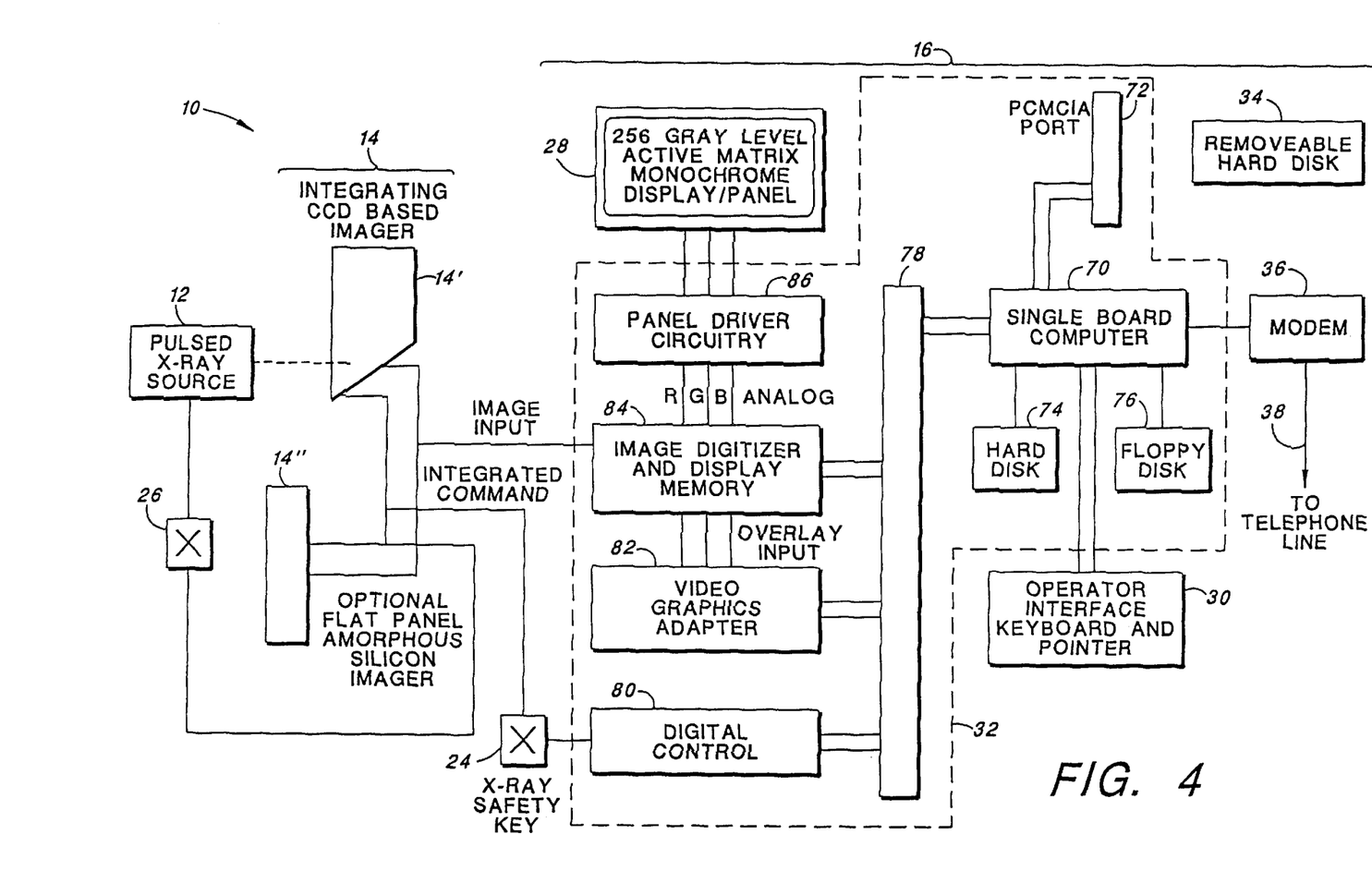
FIG. 4 is a block diagram of the imaging system and shows additional detail of the display/controller unit.

Turning next to FIG. 4, a more detailed block diagram of the imaging system 10, and particularly of the control unit 16, is illustrated. As seen in FIG. 4, at the heart of the control unit 16 is a single board computer (SBC) 70. The SBC 70 is connected in conventional manner to a PCMCIA port 72 (adapted to interface with a removable hard disk 34), a hard disk 74, a floppy disk drive 76, a keyboard/pointer 30, and a modem 36, all of which are of conventional design. The SBC 70 further interfaces, through a suitable bus 78, with digital control circuitry 80 (for generating/interfacing the digital control signals that are sent to the imager 14 and the X-ray source 12), a video graphics adapter 82 and an image digitizer and display memory 84, all of which may also be of conventional design, except as indicated below. The image digitizer and display memory 84 further interfaces, through panel driver circuitry 86, with an active matrix monochrome display panel 28. Advantageously, all of the components of the control unit 16 are effectively those of a conventional personal computer (PC), with some modifications, as explained below.

While any suitable PC could be used and modified for use with the invention, the preferred PC is at a minimum a 486 class microprocessor, or better, operating at a preferred minimum clock speed of about 33 MHz, and modified as required to drive the active matrix monochrome display panel 28 so that it exhibits a large gray scale resolution, e.g., a gray scale that provides 256 different shades of gray. Such gray scale resolution is generally not commercially available, to applicant's knowledge, particularly in a small, transportable, ruggedized, self-contained, has-the-appearance-of-a-suitcase, unit. When modified, as explained below, the unit 16 has dimensions of only 18 by 13 by 7 inches, weighs only about 24 pounds (including a battery pack), and is housed in a "suitcase" housing that, when closed, does not readily identify its function. Such disguised appearance can be an important feature for some applications of the invention so that the unit can be easily carried into a desired field location, e.g., a busy airport terminal, without initially drawing undue attention thereto.

As indicated, most of the components of the control unit 16 are conventional components that may be provided by any suitable computer manufacturer. The principal exception to his general availability is the active matrix display 28 and associated driver 86. The use of a flat panel display 28 is very desirable for a portable system from a portability and ruggedness perspective. Advantageously, the use of a TFT flat panel display is particularly suited for the imaging system 10 because of the available brightness and wide range of available colors and grayscales. Disadvantageously, the use of TFT flat panel devices is complicated by the fact that they are relative recent additions to the display market, and the interface electronics to drive these displays, particularly for a monochrome application where a high grayscale resolution, e.g., 256, is desired, is not yet available. To further complicate matters, the signal to be displayed for the imaging system 10 is an analog VGA video signal, rather than a digital drive signal as is customarily used to drive such displays.

Figure 6:
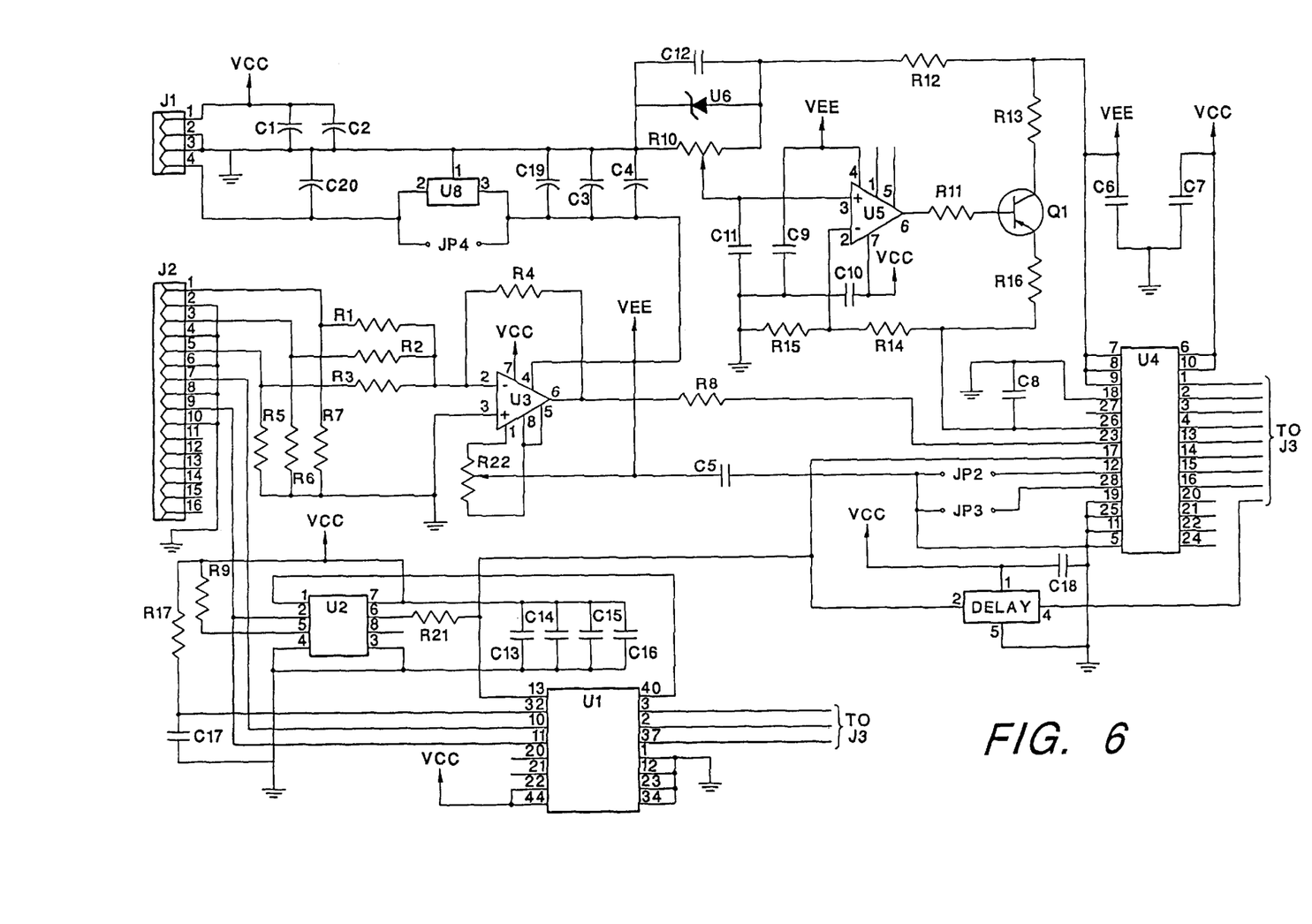
FIG. 6 is a schematic diagram of the panel driver circuitry of FIG. 4.

In view of the above difficulties, the present invention uses a custom panel driver circuit as shown in FIG. 6. The circuit in FIG. 6, explained more fully below, performs the function of converting the standard VGA signal, with its three component signals, red (R), green (G), and blue (B), to a digital signal suitable for driving the TFT active matrix flat panel display 28.

The preferred active matrix flat panel display for use with the control unit 16, but certainly not the only flat panel display that could be used, is a LDH096T-11 display made by Flat Panel Display Co. of Eindhoven, The Netherlands. The LDH096T-11 is a 9.5 inch diagonal LCD module that comprises an Active Matrix Liquid Crystal Display, an integrated adjustable backlight and module electronics. The module electronics facilitate interfacing with commercially-available VGA chipsets, and can display either 16 or 256 levels of gray depending on user selection. The display resolution of the LDH096T-11 is 640 by 480 dots, with a dot pitch of 300×300 μm. The contrast ratio is better than 60:1 at optimum viewing angles, and the brightness is 60 cd/m$^2$.

The active area of the display is 192 by 144 mm. The power consumption, including backlight, is only about 2.5 Watts (nominal). The supply voltage for the display is 5 volts.

The panel driver circuit used to drive the LDH096T-11 display is shown in the schematic diagram of FIG. 6. The main signal inputs to the circuit shown in FIG. 6 comprise the RGB signals from the analog VGA signal, which signals are applied to connector J2 and directed to amplifier/summer U3, where they are multiplied by an appropriate gain factor and summed. The summing of the three RGB signals combines the signals, putting them on a single signal line (the output of amplifier U3). This summed/combined signal is then applied to analog-to-digital (A/D) converter U4, which converts the signal to an appropriate digital signal that can be applied to the display 28 through connector J3. The necessary clock signals and control signals needed by the A/D converter U4 and the flap panel display via connector J3 are generated in the programmable array logic contained in device U1. Other components, as well as control, timing and voltage signals, used within the circuit shown in FIG. 6 should be self-evident from the schematic diagram of FIG. 6 to those skilled in the electronic arts.

A preferred control unit 16 for use with the present invention comprises a modified SafeCase® Series 4000 Rugged Portable Computer made by Industrial Data Systems, Inc., 14900 Woodham Drive, Building 170, Houston, Tex. 77078-6016. The Series 4000 computer is ordered to include an 80486 microprocessor with a clock speed of 33 MHz, 8 MB of RAM, a 3.5" high density floppy disk drive, and at least a 210 MB hard drive. The basic unit offered by Industrial Data Systems (IDS) as specified above is further modified for 120/220 VAC 50/60 Hz/12 VDC operation, including a battery charger that charges the battery automatically whenever the unit is connected to a 120/220 VAC power line. To enhance battery operation, a Microbus MAT 752 low power 486DX/33 CPU board is installed in the unit 16 as the SBC 70. WIth such low power CPU board, a fully charged battery pack permits 75 to 80 minutes of operation of the unit. The charge level of a given battery pack can be tested at any time using a built-in push button and LED display located at the lower right corner of the battery pack. The battery packs may also be charged external to the unit 16 using a suitable battery pack charger.

As additional modifications to the Series 4000 Portable Computer, an Interlink Durapoint mouse pad pointing device, or other pointing apparatus, is built into the top panel the case (or otherwise made available to the user). Preferably, such pointing apparatus is positioned to be centered just below the keyboard so that a user can manipulate it with his/her thumbs while keeping his/her fingers on the keyboard. A PCMCIA Type III connector is also added to the top panel, and the Microbus CPU Board is connected to drive this port. It is through this port that removable storage media, or other peripherals, may be connected to the Microbus CPU Board. In addition, the I/O (input/output) expansion plate of the unit is punched to accept an Amphenol #165-159236 connector and cable, which when installed and connected to the Microbus CPU Board, functions as the connector for the long cable 18. The LCD panel is modified to accept the above-described FPD LDH096T-11 display 28, and the panel driver circuitry 86 (shown in FIG. 6) is appropriately installed within the unit 16 so as to drive the display 28 as controlled by the Microbus CPU board. Also installed in the unit 16 is an internal modem and external RJ-11 jack to facilitate modem communications.

The image digitizer and display memory 84 (sometimes referred to herein as simply the "image processor" 84) comprises a separate or auxilliary processor installed within the control unit 16 in order to facilitate the receipt, processing, and display of the integrated signal from the imager 14. Such image processor 84 may take several forms, and there are numerous commercially-availalble processor boards that could be used for this purpose. At the present time, one of two commercially available processors is preferred for use as the image processor 84, both of which are manufactured and sold by Matrox Electronic Systems, Ltd., 1055 St. Regis Blvd. Dorval, Quebec, Canada H9P 2T4. A first preferred processor is the Matrox Image-LC image processor, which is designed to interface with a wide range of analog and digital devices. The Matrox Image-LC processor, the operator's manual for which is incorporated herein by reference, is a programmable processor that is very versatile, and provides a great many options, such as the ability to perform mathematical computations on a pixel by pixel basis at the processor 84 (as opposed to being performed at the SBC 70). The result is very fast image processing. Because the Image-LC processor is a very capable and fast processor, it is also somewhat expensive and consumes a significant amount of power.

A second preferred processor for use as the image processor 84 is the Matrox IP-8 Frame Grabber. The Matrox IP-8 Frame Grabber, the operator's manual for which is also incorporated herein by reference, is a flexible, low-cost monochrome frame grabber and display processor that offers only a few of the processing features of the Image-LC processor. However, the IP-processor still offers sufficient processing capability for most applications of the present invention. For this reason, and given its lower-cost, and less power consumption, the IP-8 Frame Grabber is the image processor that is generally used most often with the present invention.

The Video Graphics Adapter (VGA) 82 of the control unit 16 comprises a standard VGA board, as is used in any personal computer providing VGA graphics.

The digital controller 80 of the control unit 16 functions to provide an appropriate isolated interface between the control unit 16 and the imager 14 and X-ray source 12 relative to the trigger or synchronization signals that must be sent to the imager 14 and X-ray source 12. More particularly, for the preferred X-ray source 12 and imager 14 described above, the controller 80 produces a TTL (transistor-transistor logic) electronic synchronization signal which when driven to a ground potential accomplishes both (1) the firing of the X-ray source 12, and (2) the integration of the image signal at each pixel site within the imager 14. When the TTL signal is returned to +5 VDC, the X-ray source is inhibited, and the integrated signal is read out of the imager 14 after the next video vertical interrupt. The net result (and desired goal) is that the rapid read out of the video signal from the imager 14 is properly synchronized with the digitizer of the image processor 84.

As seen in FIGS. 1, 2 and 4, the X-ray source 12 is connected to the control unit 16 through the imager 14. That is, the long cable 18 is connected between the control unit 16 and the imager 14, and the short cable 20 is connected between the imager 14 and the X-ray source 12, and there is not direct cable connection between the control unit 16 and the X-ray source 12. An isolation relay is used at the imager 14 to apply a trigger (or "fire") signal to the X-ray source 12 through the short cable 20 as soon as the TTL synchronization signal is pulled low (or no longer than one frame time thereafter, where one frame time is, e.g., the vertical blank interrupt period, typically 1/60 of a second). The X-ray source continues generating its burst of X-ray pulses until the TTL signal goes high (or until no longer than one frame time after the TTL returns to +5 VDC). Advantageously, use of the isolation relay keeps electrical noise from getting into the video signal or affecting the stored image on the CCD chip. Thus, it is seen that the imager 14 is enabled (its "shutter" is open to receive an image) at the same time as, or perhaps even just slightly before, the X-ray source 12 provides its burst of X-ray pulses, and remains enabled for so long as, or perhaps even just slightly longer than, the burst of X-ray pulses ends. After completion of the exposure, i.e., within one frame time thereafter, the integrated signal acquired at the imager 14 is downloaded to the image processor 84, and is thereafter available for display at the active matrix display 28 and/or for storage within any of the available storage media used by the control unit 16.

Advantageously, because the control unit 16 is based on a PC-type digital computer, and because of the conventional components used within such computer, both in terms of hardware and software, it is capable of accomplishing a wide variety of image acquisition, manipulation and data storage tasks. Many of these tasks may take advantage of recent advances in Graphical User Interface (GUI) technology, particularly in view of the fact that the familiar MICROSOFT (MS) Windows operating system is being used. For example, with hardware which supports "Digital Chromoakeying", it is possible to superimpose images stored in the memory of the image acquisition memory buffer with the MS Windows desktop display. Such capability provides a very compact and convenient user interface.

Further, because PC-based technology is used within the control unit 16, there exists great flexibility in how the resulting data is stored and transmitted. For example, the conventional TIF binary file format, commonly used for faxes, drawings, and other graphical (digitized) displays/images in the PC-based environment, may be used to store and manage the digitized images. Fortunately, a significant body of commercially-available software exists to aid in the handling, storage, and management of such displays. In addition, such TIF images can be copied to a standard 1.44 MB floppy diskette, using the floppy disk drive included as part of the control unit 16, or to a standard removable hard drive (which has the capacity to store hundreds of such images) using the PCMCIA port, or transmitted via the modem 36. As a result, the images can be transported, transferred and/or copied onto any other PC compatible system. Such images can then be viewed, manipulated, and/or printed using one of the numerous graphics and desktop imaging programs which are commercially available.

The control unit 16 stores the digital image in a frame buffer memory that forms part of the image processor 84 (FIG. 4). Such storage of the image allows the host computer, i.e., the SBC 70, and/or the image process or 84 (if the image processor has such capability) to perform mathematical calculations, on a pixel-by-pixel basis, in order to enhance and emphasize particular details in the X-ray image. When the image processor 84 has the capability to perform such calculations, as does, e.g., the Matrox Image-LC processor board referenced previously, then such pixel-by-pixel calculations can be completed very rapidly. When the image processor 84 lacks this capability, as does, e.g., the Matrox IP-8, the calculations can still be performed by the SBC 70, but they are not completed near as quickly.

Among the types of mathematical calculations that may be performed on a pixel-by-pixel basis are various convolution techniques, accessible through commercially-available software, that modify the displayed image to produce a variety of effects. These effects include: (1) fine sharpening, which subtly increases the clarity of an image by enhancing high frequency components, making edges of objects appear sharper; (2) coarse sharpening, which is a variation of fine sharpening, but which produces a more dramatic noticeable sharpening; (3) smoothing, which reduces the "grainy" appearance of an image having excessive high frequency noise; (4) horizontal edge detection, which suppresses (i.e., turns black) all pixels in an image except for those which form horizontal edges of objects in the image, thereby causing such horizontal edges to appear white, and making them stand out in high relief; and (5) vertical edge detection, which does the same thing to vertical edges that the horizontal edge detect does to horizontal edges.

It is noted that other mathematical operations and functions could also be used in addition to, or in lieu of, the above listed convolution techniques in order to sharpen and enhance a given image. For example, multiple image arithmetic calculation functions, (i.e., pixel-to-pixel Addition, Subtraction, Multiplication, Division, And, Or, Xor, etc.), Blob Analysis, Pattern Analysis, Fast Fourier Transforms, and other more extensive convolution techniques, could be performed.

Moreover, in addition to mathematical manipulation, the control unit 16 permits a wide variety of display flexibility, which also enhances the desired details of an acquired image. For example, zooming by factors of 2 and 4 are supported, allowing small details to be magnified and viewed in greater detail. Panning and scrolling functions are also available in conjunction with the zoom capability to allow a user to move about within the magnified image. A contrast stretch function, discussed in more detail below, is further provided which interactively allows the user to change the displayed contrast and brightness of specific grayscale regions of the image. Such contrast stretch function is particularly useful for increasing the brightness and clarity of very dense objects.

An invert function is likewise provided within the control unit 167 which changes the image from a black-to-white "positive" image into a white-to-black "negative" image. Such function aids radiographers who are more comfortable viewing images as they would appear, e.g., on X-ray film.

As indicated, the control unit 16 preferably operates in a Windows-based mode, thereby providing an operator of the system, once the system has been set up and turned on, the ability to select various options related to the imaging task at hand. Such options are controlled by appropriate applications software that is stored on the unit's internal hard drive.

Figure 7:
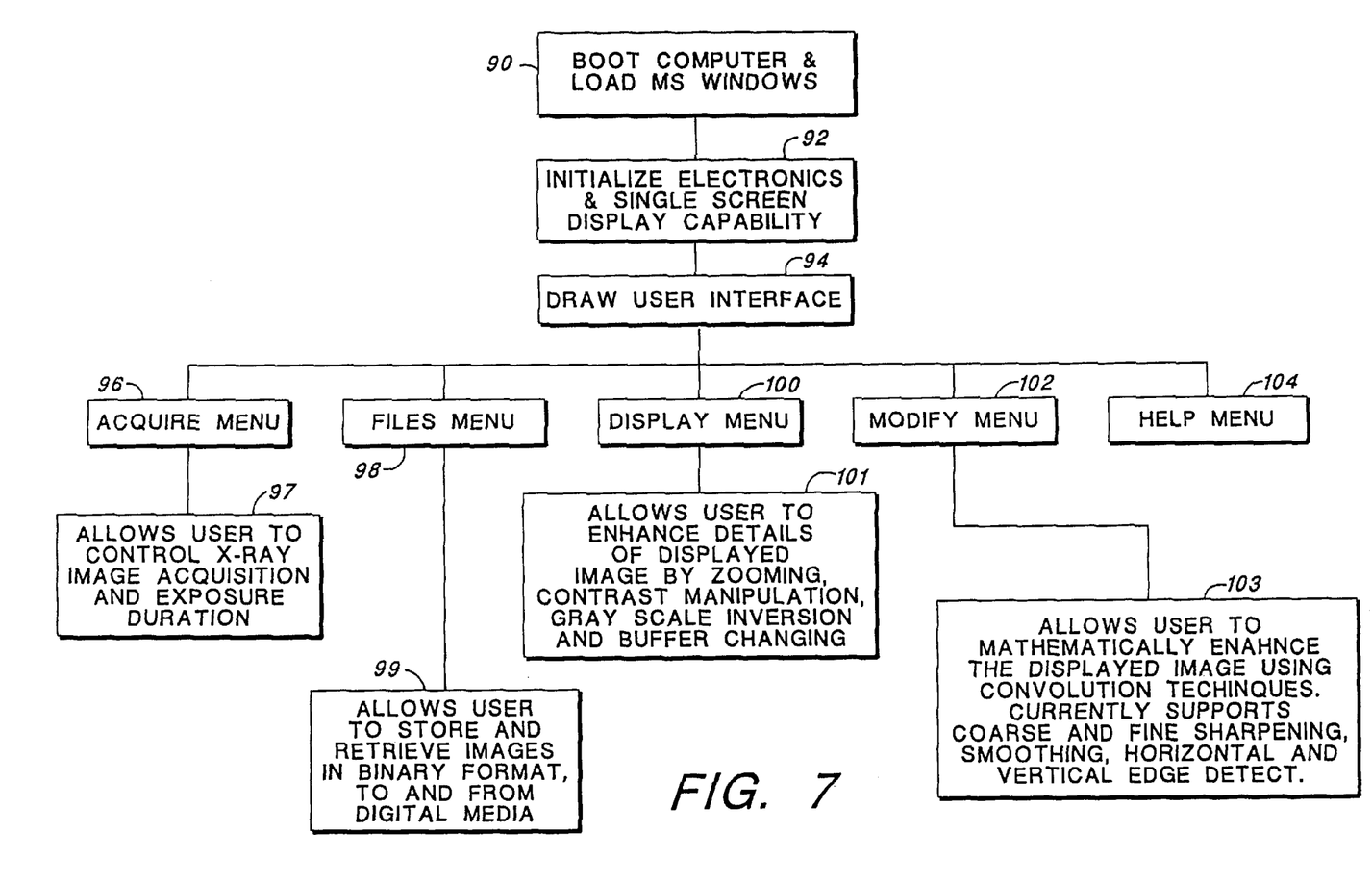
FIG. 7 depicts the various software modules that may be invoked by a user of the imaging system of FIGS. 1 and 2.

A flow diagram of the software control used within the unit 16 is illustrated in FIG. 7. As seen in FIG. 7, when power is first applied to the unit, the computer is booted on and Microsoft Windows is loaded (block 90, FIG. 7). The electronics of the image processor 84 are then initialized, power-on diagnostics are performed, and the single screen display capability is verified (block 92). Once initialized, a User Interface Main Menu is drawn on the screen (block 94) using a conventional windows format.

The User Interface Main Menu screen allows the user to select one of five options. A first option (block 96, FIG. 7) allows the user to get ready to acquire an image. Such option (as indicated at block 97) provides the user with an acquire menu that allows the user to control the X-ray image acquisition and exposure duration. Further details associated with the selection of the "Acquire" option are presented below.

A second option (block 98) provides the user with a "files" menu. The files menu allows the user to store and retrieve images in binary format to and from digital media (block 99), e.g., an internal hard drive, a floppy disk, or a removable hard drive.

A third option (block 100) provides the user with a "display" menu. The display menu allows the user to enhance details of the displayed image (block 101) by, e.g., zooming, contrast manipulation, grayscale inversion, and buffer changing.

A forth option (block 102) provides the user with a "modify" menu. The modify menu allows the user to mathematically enhance the displayed image (block 103) using convolution techniques. Such mathematical enhancements include, at the present time, coarse and fine sharpening, smoothing, and marking horizontal and vertical edge detection.

A fifth option (block 104) provides the user with a "help" menu. The "help" menu provides the user with whatever information may be helpful to the user, e.g., a further description of the other options, the latest enhancements that have been included in the software, and/or any other information that helps the user debug any problems he/she may be experiencing with the operation of the system 10.

Figure 8A:
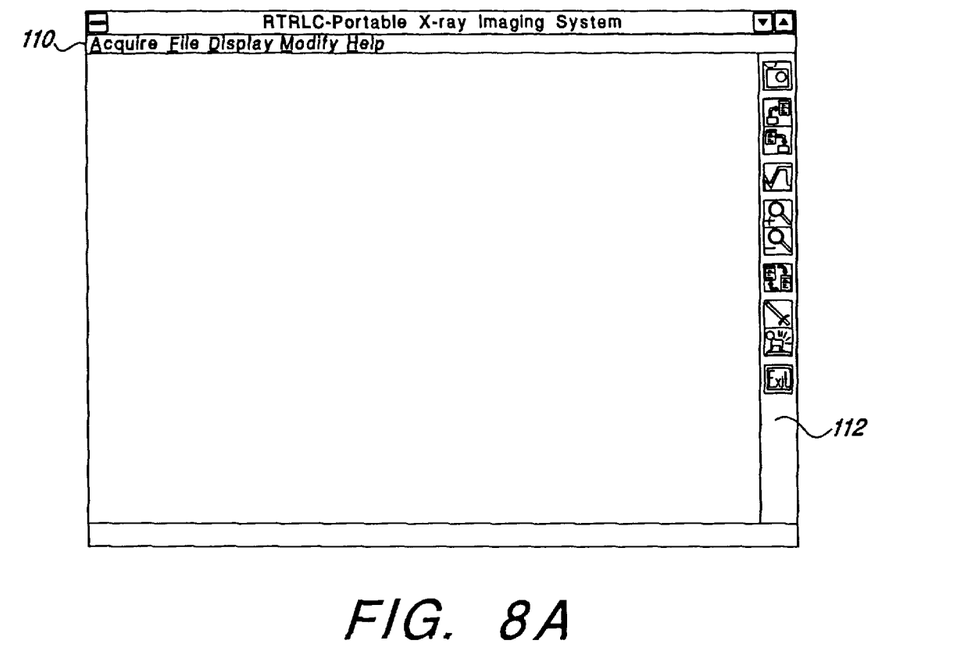
FIGS. 8A, 8B and 8C respectively depict various windows or "screens" that are displayed to a user as different control options are selected.

A representation of the User Interface Main Menu is presented in FIG. 8A. This menu is displayed on the display screen 28. Note that the Main Menu appears as a conventional "window" for use within a Microsoft windows environment. There is a menu bar 110 located across the top of the screen, and a column of icons 112 located on the right of the screen. From this main Windows menu, the user can access the various options provided by pull-down menus or icons associated with each option. The functions which can be activated by the icons are a subset of the functions which can be accessed through the pull-down menus.

As with any Windows environment, selection and activation and/or initialization of each of the various activities represented by the corresponding icons or pull-down menu options is made using the arrow cursor displayed on the flat panel display, or by using keyboard selections consistant with the standard Windows applications. That is, a function represented by an icon is activated, e.g., by simply moving the arrow cursor to the point within the appropriate icon using the mouse (or other pointer device) and pressing (or "clicking") the left button on the mouse, or moving the arrow cursor to the named menu item on the menu bar and pressing the left mouse button. Alternatively, the "Alt" key may be pressed simultaneously with the first (or underlined) letter of the named menu item on the menu bar.

Figure 8B:
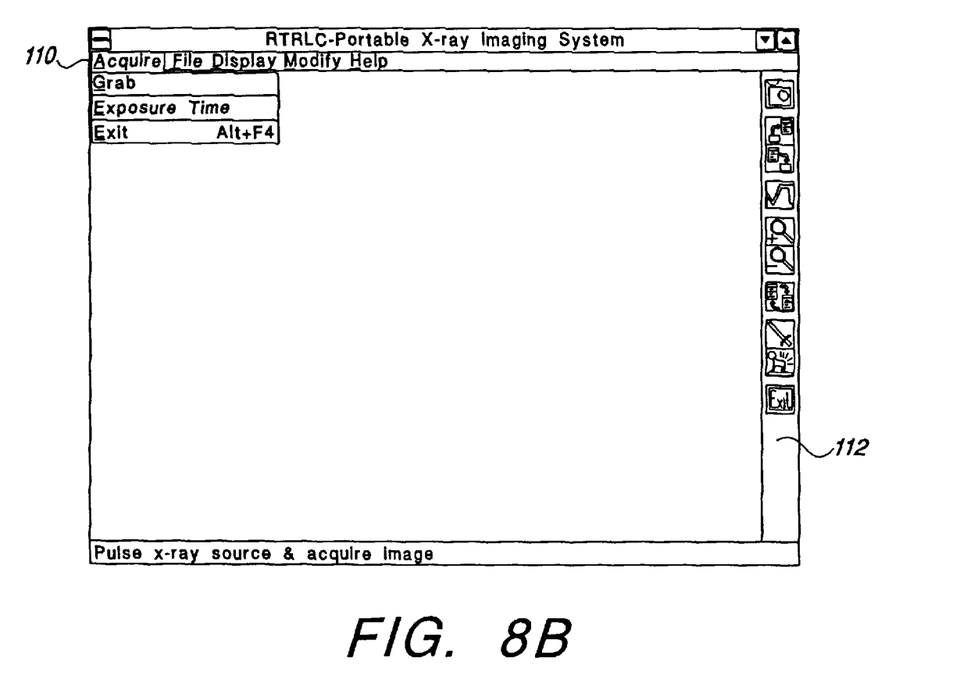

To illustrate, an X-ray image is acquired by moving the arrow cursor and pointing-and-clicking on the Acquire option on the menu bar 110, or equivalent icon in the icon column 112. Such action causes the Acquire pull-down menu to be activated, as represented in FIG. 8B. The Acquire pull-down menu lists three options, as shown in FIG. 8B, including "Grab", "Exposure Time", and "Exit". An image acquisition is referred to as a "grab" because it entails pulsing the X-ray source 12 and "grabbing" the video data resulting therefrom which make up the radioscopic image.

Figure 8C:
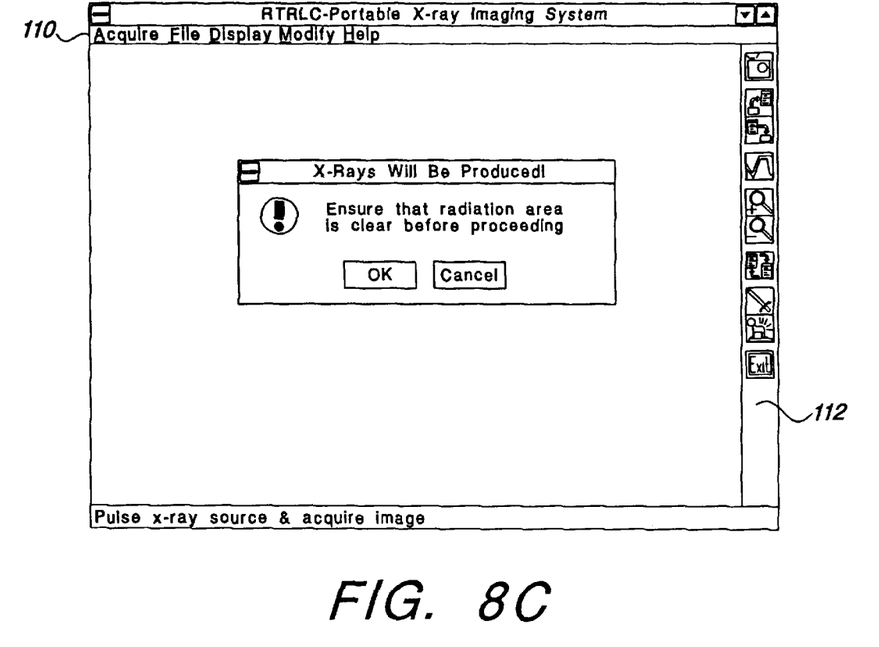

Once the Grab option has been activated, a dialog box appears in the center of the Display Panel as shown in FIG. 8C. This dialog box serves as a safetyfeature, or software interlock, that warns the operator that X-ray production will be initiated by the next step, and that the X-ray beam area should be clear of all personnel.

As seen in FIG. 8C, two options are provided below the warning: (1) to produce X-rays and acquire an image, the user must use the mouse to point-and-click on the OK button; or (2) the grab request can be cancelled by using the mouse to point-and-click on the Cancel button, which returns the user to the Acquire pull-down menu (FIG. 8B). When the user selects the OK option, the X-ray source pulses immediately and an image forms on the display panel 28. This image is the radioscopic image that is created by having X-rays directed at and pass through the object 22, as sensed by the imager 14, and processed by the circuitry within the control unit 16. Advantageously, at the completion of the Grab sequence, the system returns to the Acquire pull-down menu, and the acquired radioscopic image is displayed beneath the menu overlay graphics.

As mentioned previously, there is an interlock key 24 located on the control panel of the control unit 16, and another interlock key 26 located on the X-ray source. These interlock keys are intended to enhance radiation safety. Both of these keys must be in place and turned to the ON position in order for X-ray production to occur. If either of these keys is not in place and in the ON position, the X-ray source will not fire, a call to the Grab function will time-out, and the system will return to the Acquire pull-down menu without creating a radioscopic image.

Once an image has been acquired, the user may select other menu bar or icon bar options depending on what is to be done next. If the acquired image is not quite right, e.g., due to under or over exposure, or the feature(s) of interest in the image are not properly oriented for definitive evaluation, another image may be acquired after appropriate adjustments are made to the image acquisition time. Such adjustments are made using the Exposure option in the Acquisition pull-down menu, or by adjusting the X-ray source/target/imager geometry. If the quality of the image just acquired is satisfactory, the image can be stored to hard disk or floppy disk using the options found in the File pull-down menu. Further, an acquired image can be visually manipulated using the functions found in the Enhance or Modify pull-down menus. For example, an image which has just been acquired will usually benefit from the Sharp 1 or Sharp 2 enhancements presently offered as the first and second options, respectively, in the Modify menu. These edge sharpening options use the image processor's capabilities to make the acquired image appear sharper than the original image. It is to be emphasized, of course, that the use of such edge shapening options are meant to be exemplary, not limiting.

A more thorough description of the various User Interface options is found in Appendix A of applicants' prior patent, U.S. Pat. No. 5,608,774, which patent is incorporated herein by reference. In Appendix A, of U.S. Pat. No. 5,608,774 the imaging system 10 is referred to as the "RTR-3", which is the name its manufacturer, Science Applications International Corporation (SAIC), of San Diego, Calif., and assignee of the present application, intends to use when marketing the invention.

One particular image enhancement feature of note is the Contrast Stretch option available through the Display pull-down menu. The Contrast Stretch option of the Display menu is used to change the grayscale level distribution of the displayed radioscopic image to facilitate visualization and evaluation by the operator of features of particular interest. This Contrast Stretch option is a particularly valuable option for the present invention due to the large range of grayscale resolution that is available with the display 28. As indicated previously, the display 28 preferably includes the capability of providing 256 different levels or shades of gray, ranging from black to white, within the displayed image. For example, a pure black pixel is represented by a gray scale of 0, while a pure white pixel is represented by a gray scale of 255.

A mapping function is used to map a given intensity (e.g., number of X-ray pulses received at a given pixel site) to a given grayscale value. Thus, for example, a pixel value of 0 (black) means that no radiation was sensed at the given pixel, whereas a pixel value of 255 (white) indicates that a maximum radiation level was sensed at the pixel site.

In the preferred embodiment, the mapping function that relates the sensed intensity of a given pixel site to a specified grayscale value is linear. It is to be emphasized, however, that the mapping function need not be linear, but can be any value. Performing a Contrast Stretch function changes the "slope" and "offset" of the mapping function. Slope and offset are best understood with reference to FIG. 9.

Figure 9:
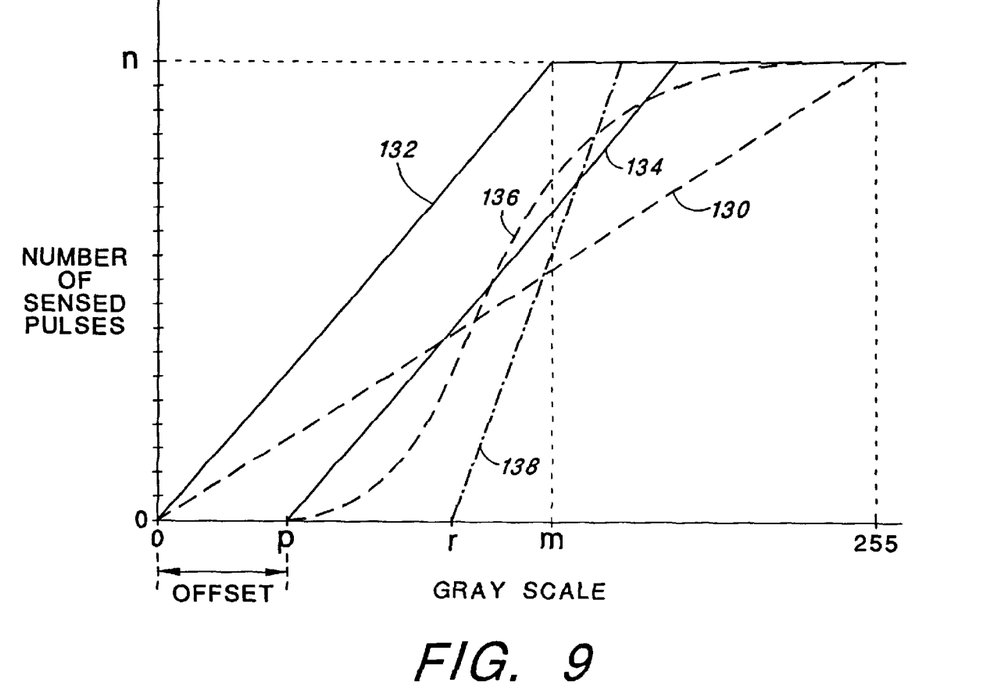
FIG. 9 graphically illustrates the manner in which the present invention achieves contrast stretching.

FIG. 9 depicts a graph that illustrates representative mapping functions that may be used to map the number of sensed pulses at a given pixel site (vertical axis) to a grayscale value (horizontal axis). Thus, for example, the dashed line 130 represents a linear mapping function with no offset and with a slope of n/255, where n represents a specified maximum number of pulses that can be sensed. The solid line 132 in FIG. 9 represents a mapping function with no offset, and having a slope of n/m where m is about ½ of 255. The slope of line 132 is thus about twice that of the line 130. Solid line 134 has a slope that is about the same as that of line 132, but with an "offset" of p, where p is an integer that is about ⅔ of m. The offset thus defines the location within the pixel value range where the linear (or nonlinear) ramp begins. The dashed line 136, for example, defines a ramp that has the same offset p as the line 134, but is not linear. Rather, the line 136 has a general "S" shape, and thus has a varying slope that is the steepest in the mid range of the number of sensed pulses. The dashed-dotted line 138 has an offset of r and a slope that is the steepest of all the lines shown in FIG. 9.

The present invention thus allows the offset and slope of the displayed image to be readily defined using, e.g., the Contrast Stretch function, and numerous other image enhancement tools described in Appendix A, of U.S. Pat. No. 5,608,774 thereby allowing the quality of the displayed image to be improved. In its present configuration, the Contrast Stretch option acts only on the output to the display panel 28. When images are stored to disk and subsequently retrieved, they will not be stretched as displayed prior to archiving. That is, saving an image to hard or floppy disk stores the data in the display memory buffer, but not the video output parameters. Nonetheless, storing and saving the video output parameters, as well as the image, is something that could be done by those of skill in the art if needed and/or desired.

The image enhancement tools used by the present invention, and described in Appendix A, of U.S. Pat. No. 5,608,774 are realized using commercially available imaging application development software. Such software may be obtained, e.g., from Matrox Electronic Systems, Ltd., of Quebec, Canada. Matrox provides, e.g., numerous software programs, including a Windows Utility, that allows a user to load, grab, create, duplicate, save, transmit, display, overlay, and/or process digital images. All of the enhancement features described in Appendix A, such as course and fine sharpening, smoothing, horizontal and vertical edge detection, grayscale inversion, contrast stretching, zooming, and buffer changing, are supported by software programs and/or hardware that are commercially available from companies such as Matrox, or other companies like Matrox, e.g., Data Translation, Inc., 100 Locke Drive, Marlboro, Mass. 01752-1192.

As described above, it is thus seen that the present invention provides a high-resolution, solid-state imaging system that utilizes on-chip light integration, thereby eliminating the need for intensifying electro-optic components, and wherein the system is based on a personal-computer controller that facilitates the acquiring, displaying, storing, enhancement, and/or transmitting of a digital image obtained with the system. Advantageously, such system is self-contained, lightweight and portable, and can easily be taken on-site to inspect whatever objects need to be examined without having to move such objects. Once an image is acquired, the image can be immediately sent as digital data over a modem, provided as part of the system, or stored on a floppy disk, or removable hard disk, to facilitate its transfer to an off-site location where the image can be faithfully reproduced for further analysis by off-site experts.

While the invention herein disclosed has been described by means of specific embodiments and applications thereof, numerous modifications and variations could be made thereto by those skilled in the art without departing from the scope of the invention set forth in the claims.

What is claimed is:

1. Radioscopic imaging apparatus for producing, storing, and displaying a radioscopic image of an object under investigation comprising:

an integrating X-ray image sensor positioned so that X-rays that pass through the object will impinge upon the integrating X-ray image sensor, said integrating X-ray image sensor comprising a scintillation screen and a flat panel, amorphous silicon, thin film transistor (TFT) photo sensor placed in direct contact with the scintillation screen, and including means for integrating the effects of X-rays that pass within a given pixel area of the scintillation screen until the accumulated effects of the integration are sufficient to produce a full-scale image signal and means for generating such full-scale image signal; and a control unit operatively coupled to the integrating X-ray image sensor, the control unit including a display screen, and further including processing means for: (a) generating control signals to control the generation of X-rays and the integrating function carried out by the X-ray image sensor, (b) processing the image signal to produce a digital image signal having grayscale pixel values that vary from 0 to at least 255, and (c) displaying an image of the digital image signal on the display screen.

2. The apparatus of claim 1 wherein the control unit further includes memory means for storing digital image signals and a modem operatively coupled to the memory means so that a digital image signal stored by the memory means may be retrieved from the memory means and sent over a telecommunication channel through the modem to a remote location.

3. The apparatus of claim 1 wherein the control unit includes a flat panel display on which a radiographic image of the object under investigation is displayed.

4. The apparatus of claim 1 wherein said flat panel, amorphous silicon, TFT is made on a substrate of ceramic or glass and includes a matrix of thin film transistors wherein each given pixel area of the scintillation screen has a respective thin film transistor and thin film sample and hold photodiode associated therewith.

5. A self-contained, electronic radioscopic imaging system for investigating an object comprising:

a remote X-ray sensor positioned on one side of the object under investigation so that X-rays originating from the other side of the object pass through the object and impinge thereon, the remote X-ray sensor including a scintillating screen in direct contact with a flat panel, amorphous silicon photo-sensor, the scintillating screen producing flashes of radiation when impinged by an X-ray, the flat panel, amorphous silicon photo-sensor including pixel integrating means for integrating the flashes of radiation to produce an integrated pixel signal for each pixel area of the scintillating screen, which integrated pixel signal represents the sum of all the flashes of radiation produced by X-rays that pass through the object in its respective pixel area over a prescribed time period; and a self-contained, display/control unit coupled to the X-ray sensor, the display/control unit including analog-to-digital conversion means for converting the integrated pixel image signal from each respective pixel area into a digital signal, digital image signal processing means for processing the converted pixel image signal from each respective pixel area and converting all such integrated pixel image signals to a full-scale digitized image signal, and a display for visually presenting the full-scale digitized image signal thereon.

6. The imaging system of claim 5 wherein the flat panel, amorphous silicon photo-sensor and scintillating screen each have approximate dimensions of at least 10.3 inches wide by 12 inches high.

7. The imaging system of claim 6 wherein the flat panel, amorphous silicon, photo-sensor is made on a substrate of ceramic or glass and includes a matrix of thin film transistors wherein each pixel area of the scintillating screen has a respective thin film transistor and thin film sample and hold photodiode associated therewith.

* * * * *